United States Patent [19]

Morawsky et al.

[11] Patent Number: 5,599,524
[45] Date of Patent: Feb. 4, 1997

[54] LOW VOC HAIR SPRAYS WITH IMPROVED SPRAY CHARACTERISTICS

[75] Inventors: Natalie A. Morawsky, Belle Mead; Gary T. Martino, Plainsboro, both of N.J.

[73] Assignee: National Starch and Chemical Investment Holding Corporation, Wilmington, Del.

[21] Appl. No.: 267,268

[22] Filed: Jun. 28, 1994

Related U.S. Application Data

[63] Continuation-in-part of Ser. No. 95,150, Jul. 21, 1993, abandoned.

[51] Int. Cl.⁶ .................. A61K 7/11; A61K 9/12
[52] U.S. Cl. .............. 424/47; 424/70.11; 424/70.1; 424/45; 424/DIG. 1; 424/DIG. 2; 424/78.02; 514/957
[58] Field of Search ................ 424/70.11, 47, 424/DIG. 1, DIG. 2, 71, 78.02, 45, 70.12, 70.1; 514/957, 63

[56] References Cited

U.S. PATENT DOCUMENTS

| | | | |
|---|---|---|---|
| 4,897,262 | 1/1990 | Nandagiri et al. | 424/78.02 |
| 5,021,238 | 6/1991 | Martino et al. | 424/47 |
| 5,077,040 | 12/1991 | Bergmann et al. | 424/70.11 |
| 5,094,838 | 3/1992 | Benson et al. | 424/47 |
| 5,152,984 | 10/1992 | Varaprath et al. | 424/70.11 |
| 5,158,762 | 10/1992 | Pierce | 424/47 |
| 5,176,898 | 1/1993 | Goldberg et al. | 424/47 |

FOREIGN PATENT DOCUMENTS

| | | |
|---|---|---|
| 0320218 | 6/1989 | European Pat. Off. . |
| 0323715 | 7/1989 | European Pat. Off. . |
| 1424002 | 2/1976 | United Kingdom . |
| 2132653 | 11/1983 | United Kingdom . |

OTHER PUBLICATIONS

Martino, G. T. et al. (1992). Spray Technology & Marketing, March issue, pp. 34–39.
Johnson, M. A. (1992). Spray Technology & Marketing, June issue, pp. 32–39.

Primary Examiner—Raj Bawa
Attorney, Agent, or Firm—William K. Wissing

[57] ABSTRACT

Hair spray compositions in aqueous based systems containing 80% or less of volatile organic compounds exhibit a loss of spray performance properties resulting from viscosity and surface tension increases. The addition of 0.6 to 5% of one or more hydrophobic additives selected from the group consisting of hexamethyl disiloxane, bisphenyl hexamethicone and isocetyl alcohol improves the spray characteristics by eliminating foaming at the spray actuator and on the hair.

3 Claims, No Drawings

LOW VOC HAIR SPRAYS WITH IMPROVED SPRAY CHARACTERISTICS

This application is a continuation-in-part of application Ser. No. 08/095,150, filed Jul. 21, 1993, now abandoned.

FIELD OF THE INVENTION

This invention relates to hair sprays containing 80% or less volatile organic compounds.

BACKGROUND OF THE INVENTION

In their most basic form, hair fixative compositions contain a film-forming polymer, which acts as the fixative, and a delivery system, which is usually one or more alcohols or a mixture of alcohol and water. In the case of aerosol delivery, the delivery system will also contain a propellant, typically a volatile hydrocarbon. Due to environmental regulations controlling the emission of volatile organic compounds (VOCs) into the atmosphere, VOC emissions have been restricted to 80% in some states, and may be restricted to 55%, by weight of the hair fixative formulation. It is foreseen that water will be substituted for the volatile organic compounds and so become a greater component in hair fixative compositions. However, many hair fixative polymers in current use exhibit a loss of spray performance properties in aqueous based systems; for example, the solution viscosity and surface tension increase, and if delivered by aerosol, the composition foams at the valve actuator and on the hair. These factors have prompted the search for additives to improve the spray characteristics of hair spray compositions that contain 80% or less VOCs.

SUMMARY OF THE INVENTION

This invention relates to a hair spray composition giving improved spray characteristics comprising by weight 2 to 20% of a hair fixative polymer neutralized to a sufficient amount to effect subsequent removability from hair, 0.6 to 5%, preferably 1 to 4%, of one or more hydrophobic additives selected from the group consisting of hexamethyl disiloxane, bisphenyl hexamethicone and isocetyl alcohol, 80% or less of one or more volatile organic compounds, and the balance of water to a total of 100%. Preferably, the hair spray composition comprises by weight at least 5% of water, more preferably at least about 20% of water.

In another embodiment, this invention relates to a method for improving the spray characteristics of a hair spray composition comprising by weight 2 to 20% of a hair fixative polymer neutralized to a sufficient amount to effect subsequent removability from hair, in an aqueous solvent containing 80% or less of a volatile organic compound, the method comprising formulating the composition with 0.6 to 5%, preferably 1 to 4%, of one or more hydrophobic additives selected from the group consisting of hexamethyl disiloxane, bisphenyl hexamethicone and isocetyl alcohol.

DETAILED DESCRIPTION OF THE INVENTION

It has been found that the addition of certain hydrophobic additives to standard hair fixative resins improves the spray characteristics of those resins when formulated into delivery systems comprising 80% or less of volatile organic compounds. Without the use of these additives in the hair spray composition, many of the standard resins, when delivered by an aerosol system, foam at the actuator valve and on the hair. Foaming is generally considered to be a function of the viscosity, surface tension, and the surface activity of the hair fixative polymer in solution; but while additives are known to reduce viscosity and surface tension, not all additives are successful in translating that reduction to improved spray characteristics in an aqueous system containing 80% or less of organic solvents. Therefore, it was unexpected that only certain additives out of those that could be expected to improve spray characteristics actually did improve the performance of the spray.

The specific additives are hexamethyl disiloxane, bisphenyl hexamethicone, and isocetyl alcohol, and these are effective at amounts 0.6 to 5% by weight of the hair spray formulation, preferably about 1 to 4%.

The hair fixative resins whose spray characteristics can be improved include most of the standard polymers known and used in the art, such as, vinyl acetate/crotonates/vinyl neo-decanoate copolymer, octylacrylamide/acrylates/ butylaminoethyl methacrylate copolymer, vinyl acetate/crotonates, polyvinyl-pyrrolidone (PVP), polyvinylpyrrolidone/vinyl acetate copolymer, PVP acrylates copolymer, vinyl acetate/ crotonic acid/vinyl propionate, acrylates/acrylamide, acrylates/octylacrylamide, and alkyl esters of polyvinylmethyl-ether/maleic anhydride, diglycol/cyclohexanedimethanol/ isophthalates/sulfoisophthalates copolymer, vinyl acetate/ butyl maleate and isobornyl acrylate copolymer, vinylcaprolactam/PVP/dimethylaminoethyl methacrylate, vinyl acetate/alkylmaleate half ester/N-substituted acrylamide terpolymers, vinylcaprolactam/vinylpyrrolidone/methacryloamidopropyl trimethylammonium chloride terpolymer, and methacrylates/acrylates copolymer/amine salt.

In formulation, some of these polymers require neutralization with an alkaline reagent to effect solubility or dispersibility into the aqueous delivery system and subsequently, after application to the hair, to effect removability with water or with shampoo and water. The amount of base used for neutralization is dependent on the carboxylic acid content and hydrophobicity of the hair fixative polymer. The levels of neutralization typically will range from 5 to 100%, depending on the acidity and hydrophobicity of the polymer. Suitable bases for neutralization of the polymer are the standard cosmetically acceptable bases known and used in the art. The preferred bases are sodium hydroxide, 2-amino-2-methyl-1,3-propanediol, dimethyl stearamine, potassium hydroxide, 2-amino-2-methyl-1-propanol, histidine, tris(hydroxymethyl)aminomethane, and triethanol-amine. The choice of the base and the degree of neutralization also affect the flexibility of the resultant hair fixative when sprayed on the hair, giving a soft or a hard hold. The choice of which base to utilize and the degree of neutralization required to achieve flexibility is within the expertise of one skilled in the art. In general, however, the amount of base for neutralization will be within the range of 0.05 to 5% based on the total weight of the composition, although it will be recognized that individual formulations may require neutralization outside this range.

The delivery system in most cases will be a blend of water and one or more volatile organic compounds acting as solvents or propellants. The total amount of volatile organic compound (VOC) content will be limited by environmental regulations, which in some cases is now mandated at 80% or less, and may soon be at 55% or less, based on the weight of the composition. Typically, the organic solvent will be a low boiling alcohol, acetal, or ketone, such as, methanol, ethanol, propanol, isopropanol, butanol, acetone or dimethoxymethane.

When an aerosol delivery system is used, the hair spray will require a propellant. Preferred propellants include ethers, such as dimethyl ether; one or more lower boiling hydrocarbons such as $C_3$–$C_6$ straight and branched chain hydrocarbons, for example, propane, butane, and isobutane; halogenated hydrocarbons, such as, hydrofluorocarbons, for example, 1,1-difluoroethane, present as a liquified gas; and the compressed gases, for example, nitrogen, air and carbon dioxide. The amount of propellant used in the hair fixative compositions of this invention may vary from about 3 to 60% by weight of the hair spray composition and preferably from about 3 to 40% by weight, based on the weight of the total composition. It should be noted that the above propellants are volatile organic compounds. However, the emission of hydrofluorocarbons and the compressed gases are not at this time subject to environmental regulations; therefore, these compounds may be formulated into the hair sprays of this invention without inclusion in the total VOC content. If a compressed gas or a hydroflurocarbon is used as the sole propellant or in combination with other propellants, it may be present in an amount up to 20% by weight of the total formulation.

Although not needed for spray performance, optional conventional additives may also be incorporated into the hair spray compositions of this invention to provide certain modifying properties to the composition. Included among these additives are plasticizers, such as glycerine, glycol and phthalate esters; emollients, lubricants and penetrants, such as lanolin compounds; fragrances and perfumes; UV absorbers; dyes and other colorants; thickeners; anticorrosion agents; detackifying agents; combing aids; antistatic agents; and preservatives. These additives are present in small, effective amounts to accomplish their function, and generally will comprise from about 0.1 to 10% by weight each, and from about 0.1 to 20% by weight total, based on the weight of the composition.

EXAMPLES

Example 1

A series of hair spray formulations were prepared comprising by weight 5% of a copolymer having a monomer composition in parts by weight of 50 parts tertiary-octylacrylamide, 25 parts methyl methacrylate, 20 parts acrylic acid, and 5 parts tertiary butylaminoethyl methacrylate (50 t-OA/25 MMA/20 AA/5 t-BAEM), in a solvent system of 33% DME (dimethyl ether), 22% ethanol and the balance of water, and 1% of one of the additives listed in Table 1. (Hexamethyldisiloxane was also tested at 4% and 5%). The free acidity of the polymer was neutralized to 90% with AMP. The hair spray formulations were tested for spray characteristics on 2 gram swatches of 10 inch European brown hair. The sprays were delivered with a Seaquist NS34 valve (0.013" vapor tap×0.013" stem orifice×0.040" dip tube diameter) having an Excell 200 Misty (0.016" orifice) actuator in a 2 second burst from a distance of six inches.

The spray characteristics were rated either positive (+) or negative (−). A positive rating indicates a wide spray cone, fine spray, small particle size, and no foam on the hair or actuator. A negative rating indicates a narrow spray cone, spitting at the actuator, large particle size, and obvious foaming on the hair or actuator. The results are set out in Table 1 and show that it is not obvious from the physical characteristics of the hair spray formulation (surface tension and viscosity) to predict which additives would give superior spray characteristics. The results also show that out of a wide variety of potential additives, only three actually improved the spray characteristics of a 55% VOC hair spray.

TABLE 1

| | Spray Characteristics | | |
|---|---|---|---|
| 1% Additive | Brookfield Viscosity[a] | Surface Tension dynes/cm[b] | Spray Characteristics |
| hexamethyldisiloxane | 6 | 25.1 | + |
| (at 4%) | | | + |
| (at 5%) | | | + |
| bisphenylhexamethicone | 6 | 22.8 | + |
| isocetyl alcohol | 6 | 25.5 | + |
| cyclomethicone | 11 | — | − |
| isostearyl alcohol | 7 | 25.7 | − |
| methicone | 6 | 22.7 | − |
| silica silicate | 8 | 23.1 | − |
| $C_{14-18}$ isoparaffin[c] | 6 | 26.4 | − |
| cetearyl octanoate | 6 | 26.7 | − |
| dimethicone copolyol | 7 | 22.3 | − |
| phenyltrimethicone | 6 | 23.5 | − |
| octyldodecanol | 6 | 25.9 | − |
| 2-ethyl 1-hexanol | 6 | 25.5 | − |
| octyl alcohol | 6 | 25.5 | − |
| isostearic acid | 6 | 26.7 | − |
| palmitic acid | 6 | 26.7 | − |
| 2-fluorobenzyl alcohol | | | − |
| 4-fluorophenethyl alcohol | | | − |
| cetyl alcohol | 10 | | − |
| dodecyltetradecanol | | | − |
| cetrimonium chloride | | | − |
| distearyl dimethylether | | | − |
| dimethicone[f] | 7 | | − |
| phenyltrimethicone | | | − |
| trimethylsiloxysilane | 6 | | − |
| fluorochemical surfactant[d] | | | − |
| fluorinated surfactant[e] | | | − |
| propylene glycol | | | − |
| butylene glycol | | | − |

TABLE 1-continued

| | Spray Characteristics | | |
|---|---|---|---|
| 1% Additive | Brookfield Viscosity[a] | Surface Tension dynes/cm[b] | Spray Characteristics |
| lauramide DEA | | | − |
| triethylcitrate | | | − |
| polyethylene oxide glycol (PPG 24) | | | − |
| simethicone | | | − |
| hexyl alcohol | | | − |

[a]Measured with a Brookfield viscometer RVT at 50 rpm using YULA-15 spindle at room temperature.
[b]Measured with a Cenco-Dunouy tensiometer, model 70535 at 23.3° ± 0.5° C.
[c]Sold under the tradename Isopar V by Exxon.
[d]Sold under the tradename Fluorad FC129 by 3M.
[e]Sold under the tradename Zonyl FSP by DuPont.
[f]Viscosity = 10 centistokes

Example 2

A series of hair spray formulations were prepared using hexamethyldi-siloxane with a copolymer having the monomer composition in parts by weight of 50 parts tertiary-octylacrylamide, 15 parts acrylic acid, 5 parts hydroxypropyl methacrylate, 5 parts tertiary-butylaminoethyl methacrylate and 25 parts methyl methacrylate (50 t-OA/15 AA/ 5 HPMA/5 t-BAEM/25 MMA), and with a number of commercial polymers, in a solvent system of 22% ethanol, 33% dimethyl ether, and balance of water. The hair sprays were tested and rated as in Example 1 and the results recorded in Table 2. The results show that improved spray characteristics are obtained with the use of hexamethyldisiloxane.

TABLE 2

Improved Characteristics with Hexamethyldisiloxane

| Polymer | % Polymer | % HMDS | Performance |
|---|---|---|---|
| 50 t-OA/15 AA/5 HPMA/5 t-BAEM/25 MMA | 5 | 0 | − |
| | 5 | 1 | + |
| *diglycol/cyclohexanedimethanol/isophthalates/ sulfoisophthalate copolymer (45% VOC) | 15 | 0 | − |
| | 15 | 1 | + |
| *diglycol/cyclohexanedimethanol/isophthalates/ sulfoisophthalate copolymer (55% VOC) | 15 | 0 | − |
| | 15 | 1 | + |
| *vinyl acetate/crotonic acid/vinyl neodecanoate (55% VOC) | 5 | 0 | − |
| | 5 | 1 | + |
| *vinyl acetate/butyl maleate/isobornyl acrylate copolymer (55% VOC) | 5 | 0 | − |
| | 5 | 1 | + |
| *acrylates/acrylamide copolymer (55% VOC) | 5 | 0 | − |
| | 5 | 1 | + |
| *ethyl ester of PVM/MA copolymer (55% VOC) | 5 | 0 | − |
| | 5 | 1 | + |
| *vinylcaprolactam/PVP/diemthylaminoethyl methacrylate copolymer (55% VOC) | 7 | 0 | − |
| | 7 | 1 | + |
| *polyvinyl pyrrolidone (PVP) (55% VOC) | 10 | 0 | − |
| | 10 | 1 | + |
| *PVP/vinyl acetate copolymer (55% VOC) | 10 | 0 | − |
| | 10 | 1 | + |
| *octylacrylamide/acrylates/butylaminoethyl methacrylate copolymer (55% VOC) | 2 | 0 | − |
| | 2 | 1 | + |

*Identified by CTFA designation (Cosmetics Toiletries Fragrances Association).

Example 3

This example evaluates the subjective properties of a hair spray formulation at 55% VOC (33% DME, 22% ethanol, balance of water) containing 5% polymer, with and without 1% hexamethyldisiloxane. The polymer had the same monomer composition as described in Example 1. The hair sprays were evaluated on 10 inch long, 2 gram swatches of brown hair by a blind panel. Each panel member evaluated four sets of hair swatches, which contained a test swatch treated with hair spray containing hexamethyldi-siloxane and a test swatch treated with hair spray without hexamethyldisiloxane using a numerical performance rating. In the evaluations, stiffness was superior to softness; no resistance to combing was superior to resistance; no flake accumulation on hair and comb was superior to flake accumulation; gloss was superior to lack of gloss; and no static flyaway after combing was superior to static flyaway. A total of 8 evaluation sets per sample were made. The panel results were analyzed statistically (at the 95% confidence level) and summarized comparing the swatch sprayed with hair spray containing hexamethyldisiloxane as superior to (+), equivalent to (=), or inferior to (−), the swatch sprayed with hair spray without hexamethyldisiloxane. The results of the panel evaluations are set out below in Table 3 and show that the hair spray formulations performed comparably.

TABLE 3

| | Subjective Characteristics | | | | |
|---|---|---|---|---|---|
| | Gloss | Stiffness | Dry Comb | Flake | Antistatic |
| +1% HMDS | = | = | = | = | = |

Example 4

This example measures the humidity resistance of a hair spray formulation at 55% VOC (33% DME, 22% ethanol, balance of water) containing 5% polymer, with and without 1% hexamethyldisiloxane. The polymer had the same monomer composition as described in Example 1. The humidity resistance was measured as curl retention in a high humidity cabinet over a five hour period. The results are set out in Table 4 and show no statistical differences at all time intervals at the 95% confidence level.

The testing procedure was as follows: Each of the hair spray systems was tested on nine swatches of six inch strands of Remi Blue String European Brown hair, approximately 2 grams in weight, and the results pooled and averaged. Each swatch was washed in a 10% solution of shampoo, rinsed, and dried at 49° C. (120° F.). It was wet again, combed, rolled and secured onto a ½ inch diameter Teflon® mandrel, and dried at 49° C. (120° F.). When dried, it was removed from the mandrel and the resulting curl suspended.

The curl height was measured for each swatch, and then the curl was sprayed uniformly with a two second burst of the formulation per side. The curl was laid on a horizontal surface and allowed to air dry for one hour. The dried curl was then resuspended and set into a chamber at 22° C. (72° F.), 90% relative humidity, and the curl height measured immediately, and at 15, 30, 60, and 90 minute, and 2, 3, 4 and 5 hour intervals.

The percentage curl retention was calculated by the formula $(L-L')/(L-L^o) \times 100$, where L is the length of hair fully extended, $L^o$ is the length of hair before spray and exposure, and $L'$ is the length of hair after spray and exposure.

TABLE 4

| | Percentage Curl Retention | | | | | | | |
|---|---|---|---|---|---|---|---|---|
| Hair Spray with | 15 min | 30 min | 60 min | 90 min | 2 hr | 3 hr | 4 hr | 5 hr |
| 0% HMDS | 86 | 84 | 81 | 81 | 80 | 80 | 80 | 80 |
| 1% HMDS | 86 | 86 | 83 | 81 | 79 | 78 | 78 | 76 |

It should be recognized that changes and modifications in the specifically described embodiments can be carried out without departing from the scope of the invention, which is intended to be limited only by the scope of the appended claims.

We claim:
1. A hair spray composition consisting essentially of a total of 100% by weight:
   2 to 20% of a hair fixative polymer selected from the group consisting of a vinyl acetate/crotonates/vinyl neodecanoate copolymer, an octylacrylamide/acrylates/butylaminoethyl methacrylate copolymer, a vinyl acetate/crotonates copolymer, a polyvinylpyrrolidone homopolymer, a polyvinylpyrrolidone/vinyl acetate copolymer, a polyvinylpyrrolidone/acrylates copolymer, a vinyl acetate/crotonic acid/vinyl propionate copolymer, an acrylates/acrylamide copolymer, an acrylates/octylacrylamide copolymer, alkyl esters of polyvinylmethylether/maleic anhydride copolymers, a diglycol/cyclohexane-dimethanol/isophthalates/sulfoisophthalates copolymer, a vinyl acetate/butyl maleate/isobornyl acrylate copolymer, a vinylcaprolactam/polyvinylpyrrolidone/dimethylaminoethyl methacrylate copolymer, a vinyl acetate/alkylmaleate half ester/N-substituted acrylamide copolymer, a vinylcaprolactam/vinylpyrrolidone/methacryloamidopropyl trimethylammonium chloride copolymer, and a methacrylates/acrylates copolymer/amine salt,
   0.6 to 5% of a hydrophobic additive that is hexamethyl disiloxane,
   80% or less of a volatile organic compound selected from the group consisting of methanol, ethanol, propanol, isopropanol, butanol, acetone, dimethoxymethane, and dimethyl ether,
   3 to 60% of a propellant selected from the group consisting of a hydrofluorocarbon, propane, butane, isobutane and a compressed gas selected from the group consisting of compressed nitrogen, air and carbon dioxide
   0 to 10% of an ingredient selected from the group consisting of plasticizers, emollients, lubricants, penetrants, fragrances, perfumes, UV absorbers, dyes, colorants, thickeners, anticorrosion agents, detackifying agents, combing aids, antistatic agents and preservatives; and
   at least 20% of water,
      wherein the hair spray composition has improved spray characteristics compared to hair spray compositions which comprise at least 20% by weight water and which do not contain from 0.6 to 5% said hydrophobic additive.
2. The hair spray composition of claim 1 in which the hair fixative polymer comprises a monomer composition in 100 parts by weight of 30 to 60 parts tertiary-octylacrylamide, 20 to 40 parts methyl methacrylate, 10 to 25 parts acrylic acid, 0 to 10 parts hydroxypropyl methacrylate, and 0 to 10 parts tertiary-butylaminoethyl methacrylate.
3. The hair spray composition of claim 1 in which the hair fixative polymer is anionic and is neutralized with a neutralizing agent selected from the group consisting of sodium hydroxide, 2-amino-2-methyl-1,3-propanediol, dimethyl stearamine, potassium hydroxide, 2-amino-2-methyl-1-propanol, histidine, tris(hydroxymethyl)aminomethane, and triethanol-amine.

\* \* \* \* \*